United States Patent
Shyr et al.

(10) Patent No.: US 11,891,628 B2
(45) Date of Patent: Feb. 6, 2024

(54) METHOD FOR BIOMIMETIC CULTURE OF UROTHELIAL CELLS AND USES THEREOF

(71) Applicant: China Medical University, Taichung (TW)

(72) Inventors: Chih-Rong Shyr, Taichung (TW); Chi-Ping Huang, Taichung (TW); Chun-Chie Wu, Taichung (TW)

(73) Assignee: China Medical University, Taichung (CN)

( * ) Notice: Subject to any disclaimer, the term of this patent is extended or adjusted under 35 U.S.C. 154(b) by 647 days.

(21) Appl. No.: 17/053,667

(22) PCT Filed: May 14, 2019

(86) PCT No.: PCT/CN2019/086782
§ 371 (c)(1),
(2) Date: Nov. 6, 2020

(87) PCT Pub. No.: WO2019/218995
PCT Pub. Date: Nov. 21, 2019

(65) Prior Publication Data
US 2021/0095255 A1    Apr. 1, 2021

Related U.S. Application Data

(60) Provisional application No. 62/671,404, filed on May 14, 2018.

(51) Int. Cl.
*A61K 35/22* (2015.01)
*C12N 5/071* (2010.01)
*A61P 13/10* (2006.01)
*A61P 35/00* (2006.01)
*A61K 9/00* (2006.01)
*A61K 45/06* (2006.01)

(52) U.S. Cl.
CPC .......... *C12N 5/0685* (2013.01); *A61K 9/0034* (2013.01); *A61K 35/22* (2013.01); *A61P 13/10* (2018.01); *A61P 35/00* (2018.01); *A61K 45/06* (2013.01)

(58) Field of Classification Search
CPC ............................... C12N 5/0685; A61P 35/00
See application file for complete search history.

(56) References Cited

FOREIGN PATENT DOCUMENTS

CN    1638640 A    7/2005
CN    104024401 A    9/2014

OTHER PUBLICATIONS

Huang, The anti-tumor effect of intravesical administration of normal urothelial cells on bladder cancer. Cytotherapy, (20171000) vol. 19, No. 10, pp. 1233-1245 (Year: 2017).*
Roelants et al, Use of fluorescein isothiocyanate-human serum albumin for the intravesical photodiagnosis of non-muscle-invasive bladder cancer: etc. BJU International, 108 (3): 455-459, 2011 (Year: 2011).*
Huang, Chi-Ping , et al., "Xenogeneic cell therapy provides a novel potential therapeutic option for cancers by restoring tissue function, repairing cancer wound and reviving anti-tumor immune responses", Cancer cell international, published on Jan. 16, 2018, vol. 18, article No. 9, pp. 1-7, published by BioMed Central, United Kingdom.
Larsson, Hans M., et al., "Clonal, Self-Renewing and Differentiating Human and Porcine Urothelial Cells, a Novel Stem Cell Population", PLOS ONE, published on Feb. 26, 2014, vol. 9, issue 2, pp. 1-12, published by Public Library of Science, United States.
Yamamoto, Yusuke , et al., "Epithelial stem cell culture: modeling human disease and applications for regenerative medicine", Inflammation and Regeneration, published on Feb. 6, 2017, vol. 37, article No. 3, pp. 1-7, published by BioMed Central, United Kingdom.
Cross, W.R. , et al., "A biomimetic tissue from cultured normal human urothelial cells: analysis of physiological function", Am J Physiol Renal Physiol 289: F459-F468, 2005.
Wu, Wen-Jeng , et al., "National Science Council (NSC), Executive Yuan Project Report", Individual research project—NSC93-2314-B-037-057—From Aug. 1, 2004 (R.O.C. 93-08-01) to Jul. 31, 2005.

* cited by examiner

*Primary Examiner* — Qiuwen Mi

(57) ABSTRACT

The invention discloses a methodology for the biomimetic culture of urothelial cells from mammalian bladders, including murine, porcine, bovine and human sources to isolate and expand urothelial cells for use in various applications, such as intravesical urothelial cell therapy to treat cystitis and bladder cancer.

5 Claims, 12 Drawing Sheets

FIG 2A  FIG 2B
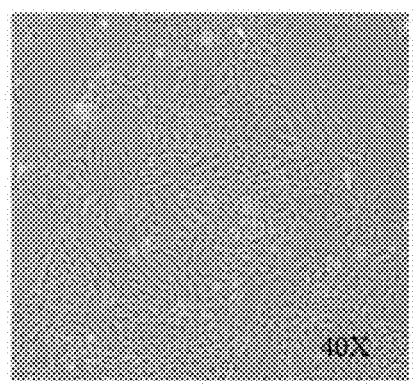 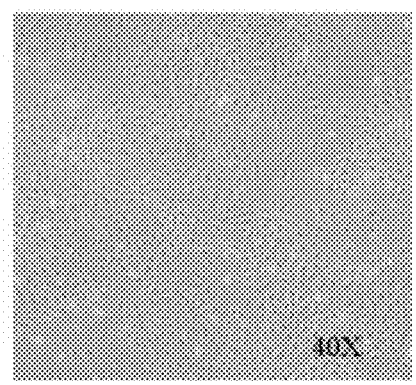
FIG. 2C
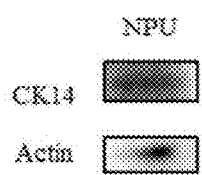
FIG. 2D
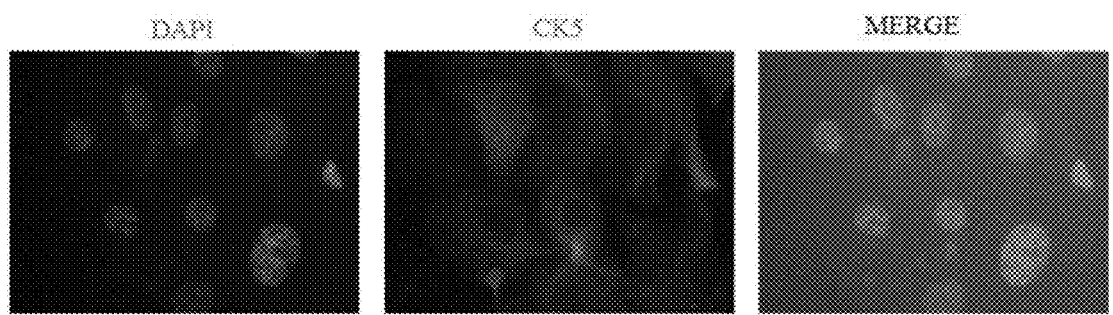
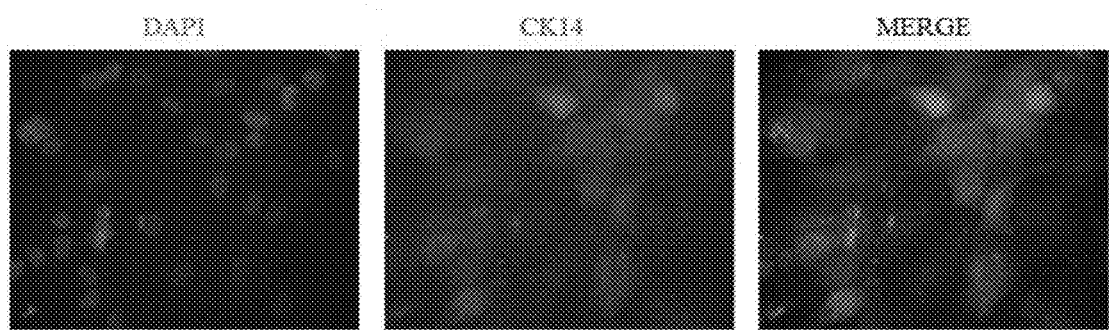

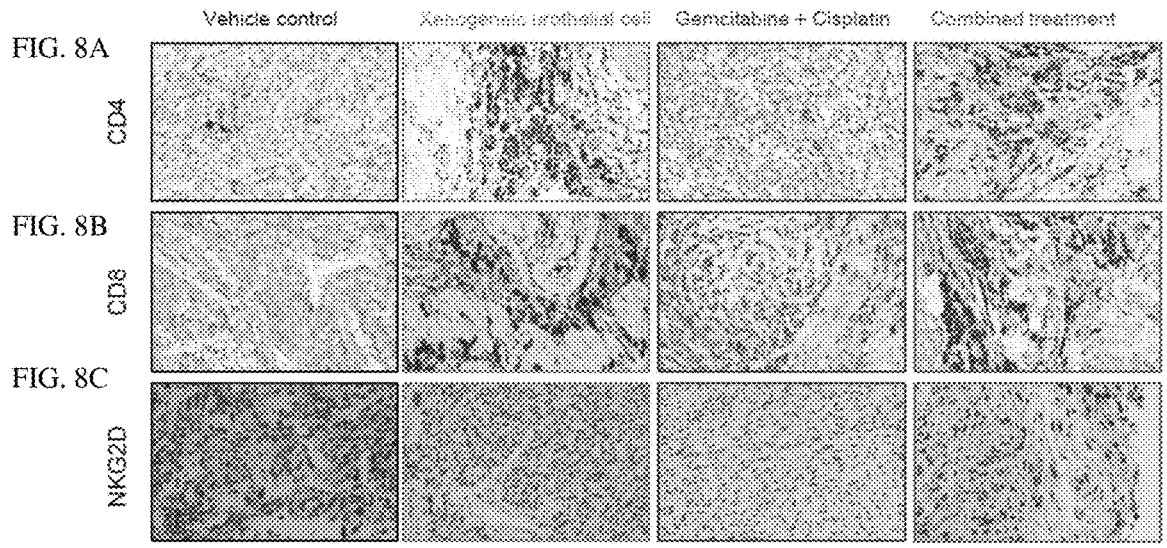
FIG. 8A
FIG. 8B
FIG. 8C
FIG. 8D
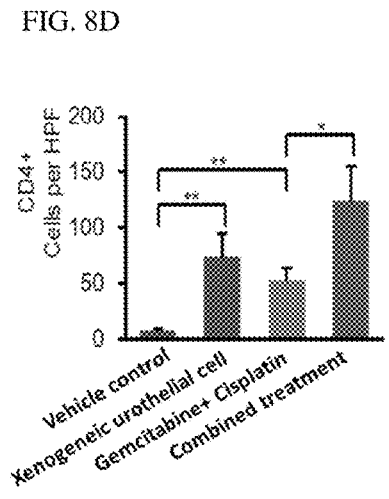
FIG. 8E
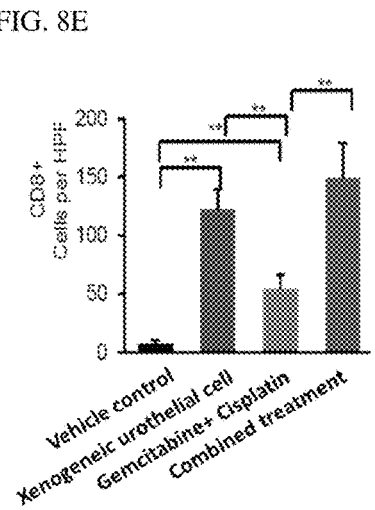
FIG. 8F
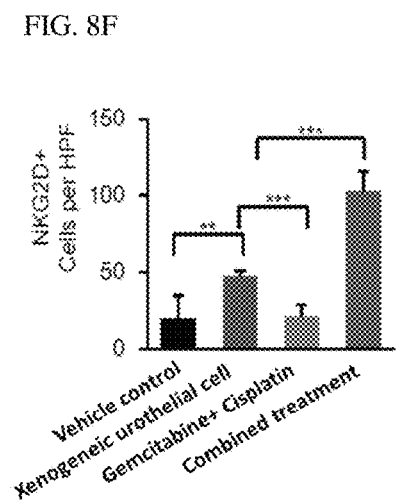

METHOD FOR BIOMIMETIC CULTURE OF UROTHELIAL CELLS AND USES THEREOF

This patent application is a U.S. National Stage Application of PCT/CN2019/086782 filed on May 14, 2019 and claims the benefit of priority from U.S. Provisional Application Ser. No. 62/671,404 filed on May 14, 2018, the contents of each of which are incorporated herein by reference in their entirety.

BACKGROUND OF THE INVENTION

Field of the Invention

This invention relates to a method and compositions for isolating and expanding mammalian urothelial cell to treat bladder related disease. Particularly, this invention relates to use biomimetic culture system to obtain urothelial cells of proliferating potential and use the isolated cells in a matrixed solution to treat urothelium dysfunction. More particularly, the invention relates to a method and composition for the treatment of bladders with urothelial injury such as cystitis and urothelial carcinoma to repair, revive and restore immune system and urothelium function. Specifically, the invention relates to a novel technique and use for repairing the damaged urothelium and reviving the immune system using xenogeneic cell source to treat cystitis and urothelial carcinoma.

Description of Prior Art

Urothelial injury such as cystitis and urothelial carcinoma could cause server morbidity even death for advance urothelial carcinoma, a major form of bladder cancer (BCa). Bladder cancer (BCa) is a common disease worldwide, which is a major cause of morbidity and mortality worldwide with estimated 429,800 cases, causing an estimated 165,100 deaths in a year 111. BCa are divided into two groups: near 75% of low-grade, papillary and usually superficial non-muscle invasive BCa (NMIBC) with a favorable prognosis vs near 25% of high-grade muscle invasive bladder cancer (MIBC) [2, 3]. Approximately 30% of newly diagnosed superficial bladder tumor are multifocal and the multifocal occurrence of bladder cancer could be explained by the "field cancerization" effect that environmental exposures to potential carcinogens account for most cases of bladder cancer, but, in the majority of cases, multifocal urothelial carcinomas are monoclonal, arising from intraluminal seeding and intraepithelial migration of a single transformed cell with variable subsequent genetic alterations [4, 5]. Initially, 60-70% of superficial non-muscle invasive BCa (NMIBC) will recur and 10-20% of them will undergo stage progression to muscle-invasive or metastatic disease [6]. Superficial bladder tumors are treated by surgical transurethral resection (TUR) of the tumor and intravesical (within the bladder) Bacille Calmette-Guérin (BCG) adjuvant immunotherapy or chemotherapy after transurethral resection of all visible bladder tumor (TURBT), but recurrence rate is still high [7]. Intravesical BCG immunotherapy using a live attenuated form of Mycobacterium bovis to treat against high risk superficial bladder carcinoma recurrences has been a standard therapeutic approach for decades [8]. The exact antitumor mechanism of intravesical instillation of BCG is unknown, but a variety of local immune responses such as the induction of CD4 T cell infiltration, which may persist for a number of months and appear to correlate with tumor suppression effect [9, 10]. Since live bacteria are introduced, BCG could cause severe cystitis and even deaths due to BCG sepsis [9]. Furthermore, for muscle invasive bladder cancer (MIBC) with radical cystectomy and systemic chemotherapy, at least 50% of these bladder cancer patients will still die from metastases within 2 years of diagnosis [2]. More desperately, the chemotherapy treatment fails in 95% of patients with less than 10% 5-year survival rate for the metastatic bladder cancer patients [2]. The reason could be that all the therapies terminate cancer cells while damaging normal cells at the same time and stimulating inflammation, thus providing opportunities for cancer cells to grow back even with a more malicious form. In US, the high recurrence rate of bladder cancer led the cost of per patient reached to $96,000 to $187,000 (from diagnosis to death, the highest of all cancer) [11] with an estimated cost of $3.98 billion in 2010 [12]. These burdens are due to the incompetence of current therapies (surgery, immunotherapy and chemotherapy) on bladder cancer. Cystitis or inflammation of the bladder, is caused by chemical, biological or physical stimuli that induce inflammation of the mucosal surface of the bladder and/or ureters [13]. Patients with cystitis may experience urgency, frequent urination of small volumes, and a painful burning sensation with urination. In addition, patients may also suffer suprapubic pain, flank or back pain. These symptoms of cystitis have a profound detrimental impact on quality of life. There are several major types of cystitis including: Hemorrhagic cystitis (HC). This type of cystitis is common in cancer patients who receive high-dose chemotherapy such as [14] and if severe, it can be fatal. In chemotherapy-induced cystitis, HC is caused by urinary excretion of acrolein, a hepatic metabolite of cyclophosphamide, which results in progressive mucosal damages. Furthermore, ionizing radiation during treatment of for pelvis neoplasms such as prostate or cervical cancer by radiotherapy may also result in hemorrhagic cystitis by injuring the urinary mucosa. However, the currently available therapies on cystitis, although effective, only provide partial solution and relief, hence there is no optimal treatment approach.

SUMMARY OF THE INVENTION

The present invention provides a method for culturing urothelial cells from a mammalian source, comprising: (a) obtaining a sample of bladder tissue from a mammalian source; (b) dissociating urothelium from mucosa layer of the sample of bladder tissue; (c) isolating dissociated urothelial cells from the sample of bladder tissue; (d) planting the dissociated urothelial cells on a biomimetic culture system; and (e) culturing the dissociated urothelial cells in a biomimetic environment and in a culture medium, wherein the dissociated urothelial cells comprises urothelial stem cells, urothelial progenitor cells, precursor cells and mature cells thereof.

The present invention also provides a method for treating a subject suffering from cystitis, urothelial carcinoma, or bladder cancer, comprising administering intravesically to the subject an effective amount of a composition comprising urothelial stem cells, urothelial progenitor cells, and cellular matrix molecules and polysaccharides.

BRIEF DESCRIPTION OF THE DRAWINGS

FIG. 2. Expanded PUC cells express urothelial stem/progenitor cell markers. (A) The representative images of PUC cells at passage 1 and 5 are shown. (B) Western blot analysis for CK5 and CK14 expression was performed on passage 3 PUC cells. (C) Immunofluorescence staining of passage 3 PUC cells was carried out with antibodies against CK5 and CK14, nuclei stained with DAPI, 400× magnification. Scale bars represent 50 µm. DAPI: 406-diamidino-2-phenylindole; PUC: porcine urothelial cell.

FIG. 8. The changes in tumor infiltrating lymphocytes and NK cells of MBT-2-luc tumor-bearing mice with different treatments. Tumors from mice given different treatments were analyzed by IHC for lymphocyte and NK cell infiltration. Representative images of anti-CD4 (A), CD8 (B) and NKG2D (C) IHC staining on tumor sections. Quantification of CD4+ T lymphocytes (D), CD8+T lymphocytes (E) and NKG2D+ NK cells (F) in tumors for each treatment group by counting the positive cells in four randomly selected HPFs among 3 mice in each group, and data were expressed as the means±SD. Error bars represent SD. *p<0.05; p<0.01; *p<0.001, by Student's t test.

DETAILED DESCRIPTION OF THE INVENTION

Figure 1A:
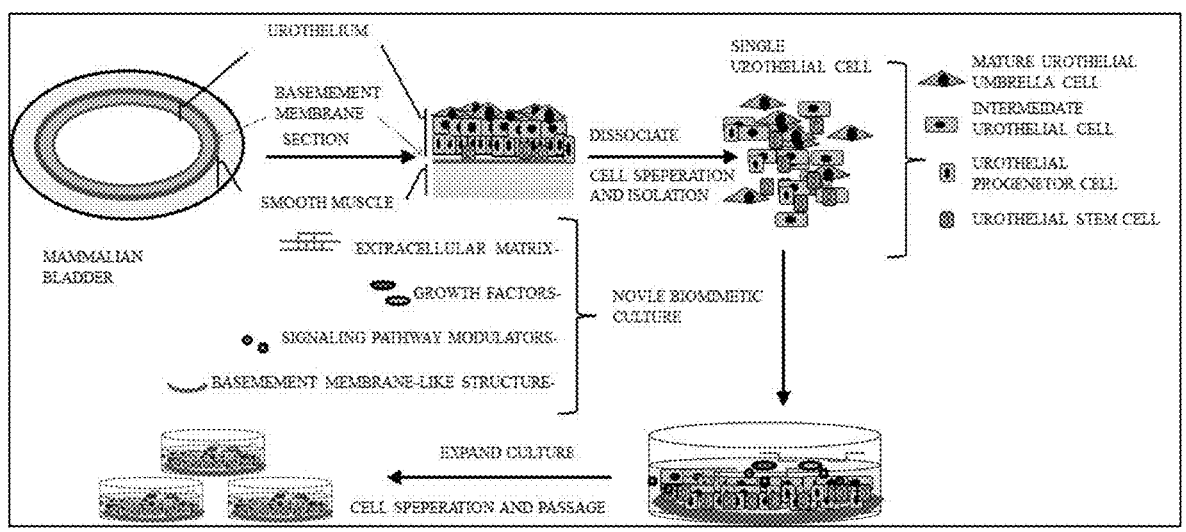
FIG. 1A shows a schematic graph illustrating an exemplary protocol for isolating and expanding urothelial cells with a biomimetic culture method for intravesical cell therapy.

The present invention provides methods for culturing urothelial cells from mammalian bladder tissue. There is a need for methods of generating normal urothelial cells for intravesical urothelial cell therapy. The present invention is directed toward solutions to address this need, in addition to having other desirable characteristics. There is a need for methods of isolating and expanding urothelial cells. The present invention is directed toward solutions to address this need, in addition to having other desirable characteristics.

In one aspect, the invention provides a method for culturing urothelial cells from different mammalian source including human, porcine, bovine and equine sources, the method comprising the following steps: The first step—The bladder tissue is removed from a mammalian source. The second step—Use enzymes and physical procedures to section urothelium from mucosa layer of bladder tissue. The third step—Isolate the dissociated urothelial cells and culture the cells in a biomimetic environment which composes a basement membrane-like support for an adherent cell culture support; and in a culture medium comprising FBS, cell matrix, growth factors and signaling pathway modulators. In the biomimetic system, dissociated urothelial cells expand with urothelial stem/progenitor cells.

The method includes contacting a cell population comprising urothelial stem/progenitor cells, precursors or mature cells thereof, with effective amount of growth factors, extracellular matrix and signaling pathway modulators for the maintaining the stem/progenitor cell population and amplifying the precursor cell population to increase the total cell number.

In accordance with aspects of the present invention, the cell precursors are selected from the group consisting of CK5/14+ urothelial stem/progenitor cells, urothelial precursor cells, and combinations thereof. In accordance with aspects of the present invention, the period of time comprises between 3 days and 10 days. In accordance with aspects of the present invention, the cell culture population contains at least 50% and 90% of urothelial stem/progenitor cells. The isolated urothelial stem/progenitor cells or population thereof expresses urothelial stem/progenitor cell marker genes.

In accordance with an embodiment of the present invention, a composition comprising the isolated urothelial stem/progenitor cells and cellular matrix is provided. In accordance with an embodiment of the present invention, a method for the treatment of a subject in need thereof is disclosed. The method includes administering intravesically to a subject in need thereof a composition comprising the isolated urothelial stem/progenitor cells and cellular matrix. In accordance with aspects of the invention, the subject has, or has an increased risk of muscle-invasive bladder cancer.

The present invention relates to a methodology for the biomimetic culture of urothelial cells from mammalian bladders of a subject. For example, the present invention also relates to a new protocol to rapidly and efficiently isolate and expand urothelial stem/progenitor cells from porcine bladders. These expanded urothelial stem/progenitor cells can be used to treat urothelial dysfunction such as cystitis and urothelial carcinoma. Previous work in the field has not used the biomimetic culture in culturing urothelial stem/progenitor cells from bladder tissue for treating urothelial injury. Previous studies only culture the cells in a 2 D environment and don't recapitulate the native growth and maintenance conditions for urothelial cells without matrix and signaling modulation.

In one embodiment, the subject is an animal. In other embodiments, the subject is a human. In other embodiments, the subject is a mammal. In some embodiments, the subject is a rodent, such as a mouse or a rat. In some embodiments, the subject is a cow, pig, sheep, goat, cat, horse, dog, and/or any other species of animal used as livestock or kept as pets.

The phenotype of the expanded urothelial cells can be determined by evaluating markers. Expression of markers can be evaluated by a variety of methods known in the art. The presence of markers can be determined at the DNA, RNA or polypeptide level. In one embodiment, the method can comprise detecting the presence of a marker gene polypeptide expression. Polypeptide expression includes the presence or absence of a marker gene polypeptide sequence. These can be detected by various techniques known in the art, including by sequencing and/or binding to specific ligands (such as antibodies). For example, polypeptide expression may be evaluated by methods including, but not limited to, immunostaining, FACS analysis, or Western blot. These methods are well known in the art.

In another embodiment, the method can comprise detecting the presence of marker gene (such as, p63, Ki-67, CK5, CK8, CK14, CK20, or a combination thereof) RNA expression, for example in urothelial cells. RNA expression includes the presence of an RNA sequence, the presence of an RNA splicing or processing, or the presence of a quantity of RNA. These can be detected by various techniques known in the art, including by sequencing all or part of the marker gene RNA, or by selective hybridization or selective amplification of all or part of the RNA.

In accordance with an embodiment of the present invention, methods for the treatment of a subject in need thereof are provided. In an embodiment, the present invention relates to treatment for bladder cystitis to repair damaged urothelium.

The methods entail administering to a subject in need thereof an isolated population of expanded urothelial cells in medium combining extracellular matrix. In some aspects, the subject has cystitis. Expanded urothelial cells generated by a method of the present invention can be intravesically administered to a subject for treatment of cystitis. In some aspects, the subject has urothelial carcinoma. In some aspects, administering to the subject comprises intravesically administered urothelial cells into the subject. The subject may be a human subject or an animal subject.

In some embodiments, the present invention relates to treatment for bladder cancer to repair damaged urothelium and revive anti-tumor immunity.

In some aspects, the method of treatment further comprises incorporating the cells into a matrix containing medium. The cells can be maintained in vitro in the matrixed medium prior to administration into the patient.

In one embodiment, the culture medium comprises bFGF. In another embodiment, the culture medium does not comprise bFGF. In one embodiment, the culture medium comprises antibiotic-antimycotic. In another embodiment, the culture medium does not comprise antibiotic-antimycotic.

In one embodiment, the culture medium comprises serum, including, but not limited to, FBS. In another embodiment, the culture medium does not comprise serum, including, but not limited to, FBS. In one embodiment, the culture medium comprises a ROCK inhibitor. In another embodiment, the culture medium does not comprise a ROCK inhibitor. In one embodiment, the culture medium comprises a BMP inhibitor. In another embodiment, the culture medium does not comprise a BMP inhibitor. In one embodiment, the culture medium comprises a WNT activator. In another embodiment, the culture medium does not comprise a WNT activator.

In one embodiment, the culture medium comprises extracellular matrix. In another embodiment, the culture medium does not comprise extracellular matrix. In one embodiment, the culture medium comprises Matrigel. In another embodiment, the culture medium does not comprise Matrigel.

In one embodiment, the expanded urothelial cells are incubated in a cell culture medium. In one embodiment, the cell culture medium is Dulbecco's Modified Eagle Medium (DMEM). In another embodiment, the cell culture medium is Dulbecco's Modified Eagle Medium/Nutrient Mixture F-12 (DMEM/F-12). In one embodiment, the cell culture medium is supplemented with fetal bovine serum (FBS).

In one embodiment, the tissue sample, for example, the urothelium sample, is dissociated into a single cell suspension. In another embodiment, the tissue sample, for example, the urothelium sample, is dissociated into cell clusters.

In one embodiment, the tissue sample, for example, the urothelium sample, is dissociated mechanically. In one embodiment, the tissue sample is dissociated mechanically by mincing with scissors.

In one embodiment, the tissue sample, for example, the urothelium sample, is dissociated enzymatically. In one embodiment, the tissue sample is dissociated enzymatically by incubation of tissue with cell culture medium supplemented with collagenase. Collagenase can break down the collagen found in tissues.

In one embodiment, the tissue sample, for example, the urothelium sample, is dissociated enzymatically by incubation of the tissue with cell culture medium supplemented with hyaluronidase. Hyaluronidase can break down the hyaluronic acid found in tissues.

In one embodiment, the tissue sample, for example, the urothelium sample is dissociated enzymatically by incubation of the tissue with cell culture medium supplemented with Dispase II. Dispase II can break down the collagen found in tissues.

In one embodiment, the cell culture medium is supplemented with collagenase hyaluronidase and Dispase II.

In one embodiment, the dissociated tissue cell suspension, for example, the dissociated urothelial cell suspension is filtered through a 40 μm cell strainer. In one embodiment, the dissociated tissue cell suspension is filtered through a 70 μm cell strainer. In another embodiment, the dissociated tissue cell suspension is filtered through a 100 μm cell strainer.

Cells can be passaged by their transfer from a previous culture to a culture with fresh medium. In one embodiment, induced epithelial cells are stably maintained in cell culture for at least 3 passages, at least 4 passages, at least 5 passages, at least 6 passages, at least 7 passages, at least 8 passages, at least 9 passages, at least 10 passages, at least 11 passages, at least 12 passages, at least 13 passages, at least 14 passages, at least 15 passages, at least 20 passages, at least 25 passages, or at least 30 passages.

In one embodiment, the cells, for example, the urothelial cells are prepared for passaging by addition of Dispase to each well. In one embodiment, the cells, for example, the urothelial cells, are passaged by addition of Trypsin to each well.

The medium also can be supplemented electively with one or more components from any of the following categories: (1) salts, for example, magnesium, calcium, and phosphate; (2) hormones and other growth factors such as, serum, insulin, transferrin, epidermal growth factor and fibroblast growth factor; (3) protein and tissue hydrolysates, for example peptone or peptone mixtures which can be obtained from purified gelatin, plant material, or animal byproducts; (4) nucleosides and bases such as, adenosine, thymidine, and hypoxanthine; (5) buffers, such as HEPES; (6) antibiotics, such as gentamycin or ampicillin; (7) cell protective agents, for example, pluronic polyol; and (8) galactose.

The urothelial cells that can be used with the present invention are prepared in a medium suitable for the particular cell or organoid being cultured. In one embodiment, the culture medium can be one of the aforementioned (for example, DMEM, or DMEM/F-12 medium) that is supplemented with serum from a mammalian source (for example, fetal bovine serum (FBS)).

In one aspect, the invention provides urothelial cells, wherein urothelial cells are obtained by the method comprising: (a) obtaining a sample of bladder tissue from a subject; (b) dissociating the urothelium; (c) isolating dissociated urothelial cells from the sample of bladder tissue; (d) plating the isolated dissociated bladder epithelial cells of (c) on a biomimetic culture system; and (e) culturing the dissociated urothelial cells in a culture medium comprising, FBS, signaling pathway modulators, and extracellular matrix molecules and polysaccharides; wherein the dissociated urothelial cells form The extracellular matrix molecules are selected from the group consisting of proteoglycans, non-proteoglycan polysaccharide, hyaluronic acid, collagen, elastin, fibronectin, and laminin.

Any of the therapeutic applications described herein can be applied to any subject in need of such intravesical cell therapy, including, for example, a mammal such as a dog, a cat, a cow, a horse, a rabbit, a monkey, a pig, a sheep, a goat, or a human.

The present invention provides a method for culturing urothelial cells from a mammalian source, comprising: (a) obtaining a sample of bladder tissue from a mammalian source; (b) dissociating urothelium from mucosa layer of the sample of bladder tissue; (c) isolating dissociated urothelial cells from the sample of bladder tissue; (d) planting the dissociated urothelial cells on a biomimetic culture system; and (e) culturing the dissociated urothelial cells in a biomimetic environment and in a culture medium, wherein the dissociated urothelial cells comprises urothelial stem cells, urothelial progenitor cells, precursor and mature cells thereof.

In one embodiment, the mammalian source is selected from human, porcine, bovine, or equine sources. In one embodiment, the dissociation is processed by enzymes and physical procedures. In one embodiment, the biomimetic culture system comprises a basement membrane-like support for an adherent cell culture support. In one embodiment, the culture medium is selected from the group consisting of FBS, cell matrix, growth factors, and signaling pathway modulators. In one embodiment, the culture medium comprises bFGF, and/or antibiotic-antimycotic. In one embodiment, the culture medium comprises serum, ROCK inhibitor, BMP inhibitor, and/or WNT activator. In one embodiment, the culture medium comprises extracellular matrix molecules and polysaccharides. In one embodiment, the extracellular matrix molecules are selected from the group consisting of proteoglycans, non-proteoglycan polysaccharide, hyaluronic acid, collagen, elastin, fibronectin, and laminin. In one embodiment, the culture medium comprises Matrigel. In one embodiment, the method further comprises contacting the dissociated urothelial cells with an effective amount of growth factors, extracellular matrix molecules, polysaccharides and signaling pathway modulators for the maintaining cell population of the urothelial stem cells or the urothelial progenitor cells and amplifying cell population the precursor cells to increase the total cell number. In one embodiment, the precursor cells are selected from the group consisting of CK5/14+ urothelial stem cells, CK5/14+ urothelial progenitor cells, urothelial precursor cells, and combinations thereof.

The present invention also provides a method for treating a subject suffering from cystitis, urothelial carcinoma, or bladder cancer, comprising administering intravesically to the subject an effective amount of a composition comprising urothelial stem cells, urothelial progenitor cells, and cellular matrix molecules and polysaccharides. In one embodiment, the method further comprises incorporating the urothelial stem cells and the urothelial progenitor cells with the extracellular matrix molecules and polysaccharides. In one embodiment, the extracellular matrix molecules are selected from the group consisting of proteoglycans, non-proteoglycan polysaccharide, hyaluronic acid, collagen, elastin, fibronectin, and laminin. In one embodiment, the composition comprises a culture medium with 5-10% dimethyl sulfoxide (DMSO).

In one embodiment, intravesical xenogeneic urothelial cell immunotherapy and GC chemotherapy combined treatment had a synergistic anti-tumor effect in the orthotopic MBT-2-luc graft bladder tumor mouse model. In one embodiment, intravesical xenogeneic urothelial cell immunotherapy and gemcitabine plus cisplatin chemotherapy combined treatment synergistically delay tumor progression in the BBN-induced bladder tumor mouse model.

EXAMPLES

The examples below are non-limiting and are merely representative of various aspects and features of the present invention.

Materials and Methods

PUC Isolation and Culture

Porcine urinary bladders for urothelial cell isolation were obtained from a local abattoir. Bladder tissue was dissected into 1-2 $cm^2$ tissue pieces and treated with dispase II dissolved in Hank's balanced salt solution (HBSS; Gibco, Carlsbad, CA, USA) to strip the urothelium. The stripped urothelium was minced into small pieces and incubated in a cell isolation solution with type VI collagenase (Worthington, Lakewood, NJ, USA) in HBSS (100 U/ml) to disaggregate the cells. Porcine epithelial cells were isolated and cultured in the Matrigel coated dish with Dulbecco's modified Eagle medium (DMEM)/Ham's F12 medium supplemented with antibiotics (penicillin 100 U/ml, streptomycin 100 mg/ml, amphotericin B 5 mg/ml), 10% fetal bovine serum (FBS), growth factor, or inhibitors of signaling pathway. Passage 2-10 cells were used in the experiments.

PUC Cell Therapy in Cyclophosphamide-Induced Cystitis

Female C3H/HeJ 9-week-old mice were obtained from Lasco (Taipei, Taiwan). To induce chemical injury-induced cystitis, the mice were intraperitoneally injected with 300 mg/kg CPP (Cayman, Ann Arbor, MI, USA) in 100 ml PBS solution. The CPP-induced cystitis mice were randomly divided into two groups: one vehicle-treated control and one PUC-treated group 4 h after CPP injection. In the vehicle-treated group, mice were subjected to intravesical instillation of vehicle and in the PUC-treated group, $10^6$ cells (passage 1 to passage 5) were intravesically instilled into bladders. Briefly, A catheter tube was introduced into the urinary bladder via the urethra, and the vehicle or PUC cells were instilled into the urinary bladder using a syringe and remained for 50 minutes, allowing the PUC cells to adhere. All mice were euthanized 20 h after the treatment and the urinary bladders were quickly removed, weighed, and fixed in 10% neutral-buffered formalin for 24 h. The tissue was cut longitudinally, routinely embedded in paraffin, sectioned and stained with hematoxylin and eosin (H&E) for histopathological examination. Alcian blue staining of urothelium glycosaminoglycan (GAG) layers was also performed to evaluate urothelial integrity. The edema score was determined by examining sections of each bladder to reflect the severity of cystitis. The score was determined as: 0=no evident sign of edema; 1=mild edema expanding the lamina propria to less than double the normal size; 2=moderate edema doubling the size of the lamina propria compared with normal; 3=moderate edema tripling the size of the lamina propria compared with normal; and 4=severe edema of the lamina propria and detrusor expanding the lamina propria more than three times the normal size. The animal protocols were approved by the institutional IACUC committee of the China Medical University.

Syngeneic Mouse Graft MBT-2-Luc Tumor Model

Female C3H/HeJ 9-week-old mice were used to establish the intramural orthotopic model. MBT-2 murine urothelial carcinoma cells stably expressing luciferase gene (MBT-2-luc) were intramuscularly injected to mouse bladder walls and capture tumor imaged by Xenogen IVIS 200 once per week. The mice are divided control and experiment groups when tumors are reached around $1 \times 10^5$ p/s total flux in bioluminescence imaging. The tumor bearing mice were divided into 4 treatment groups: (i). Vehicle control, (ii). Xenogeneic urothelial cell: intravesical of instillation xenogeneic urothelial cells ($1\times10^6$ cells), once a week, day 3 for 4 weeks, (iii). Gemcitabine plus cisplatin (GC) chemotherapy: intraperitoneal injection (IP) of gemcitabine (6 mg/mouse, day 1 and cisplatin (0.12 mg/mouse, day 2) once a week, for 4 weeks, and (iv) Combined treatment. All mouse experiments were approved by the Institutional Animal Care and Use Committees (IACUC) review board at the China Medical University. For intravesical instillation of normal xenogeneic urothelial cells, subconfluent cells are trypsinized, and greater than 90% cell viability is confirmed by the trypan blue exclusion method. Female C3H mice are anesthetized with isoflurane. Urine is void from the bladder by mild pressure on the abdomen. A 24-gauge catheter is introduced into the lumen of the bladder through the urethra. Xenogeneic urothelial cells, $1\times10^6$ in a 100 µl suspension is then injected into the bladder. To prevent voiding of the xenogeneic urothelial cells, the catheter is held in place for at least 40 minutes with the injection syringe attached. The catheter is removed before the mouse recovered from anesthesia. The responses of mice are analyzed on BLI total flux intensity changes from the baseline. The progress free survival (20% increase in tumor volume) and total survival (at the time of death or the humane endpoint: the animals exhibit severe signs of morbidity) of mice are then analyzed the total and by Kaplan-Meier's method.

N-butyl-N-(4-hydroxybutyl)-Nitrosamine (BBN)-Induced Tumor Model

For BBN-induced bladder tumor formation, a 0.05% concentration of BBN (TCI America, Portland, OR) was dissolved in drinking water, and BBN-containing water in a dark bottle was provided to 8-10 week old female C57BL/6 mice ad libitum for 10-20 weeks until hematuria score is over 2+ (Arkray Aution Sticks urine strip) as a sign of bladder tumor formation. BBN-induce tumor bearing mice were treated according to the experimental scheme in MBT-2-luc tumor bearing mice. After treatment, the bladders were harvested, weighed and examined histologically. Results were pooled from six independent experiments. Pathologic evaluation was performed on H&E stained paraffin sections of bladders, defined as follows: hyperplasia, epithelial thickening without invasion; carcinoma in situ (CIS), carcinoma cells confined to the epithelial layer; invasion, carcinoma cell invasion to the submucosal layer or muscle layer. All mouse experiments were approved by the Institutional Animal Care and Use Committees (IACUC) review board at the China Medical University.

Mixed Lymphocyte Proliferation Assay

For carboxyfluorescein diacetate succinimidyl ester (CFDA-SE) proliferation assay, lymphocytes from spleens of MBT-2-luc tumor bearing mice with different treatments were incubated for 15 min in the darkness with 5 µM CFDA-SE (Thermo Fisher Scientific, C1157, USA) in PBS and then washed. The assay was performed by co-culturing $1\times10^5$ target xenogeneic urothelial cells or MBT-2-luc cells together with $5\times10^5$ CFDA-SE-labeled lymphocytes from spleens (E/T ratio 5:1) for 2 days. The intensity of CFDA-SE fluorescence in lymphocytes was measured lymphocytes measured by using FACSCalibur flow cytometer (BD Biosciences) and analyzed with FlowJo Software.

Cytotoxicity Assay

Target xenogeneic urothelial cells or MBT-2-luc cells were labeled with CFDA-SE were plated for 24 hours and then co-cultured with effector lymphocytes isolated from the spleens of mice with different treatments at effector/target (E:T) ratio=10. After 4 hour incubation, effector cells were removed, the fluorescent intensity of remaining adherent CFDA-SE labeled targets cells were measured by a fluorimeter. The intensity of CFDA-SE labeled targets cells without co-culturing effector cells was set as the baseline. Relative cytotoxic activity of effector lymphocytes from mice of different treatment was calculated from triplicate samples as [(Baseline intensity-experimental intensity)/(Baseline intensity)] and expressed as a percentage.

Immunohistochemistry

MBT-2-luc tumors removed from the mice of different treated groups were fixed in formalin and embedded in paraffin and paraffin sections were stained with anti-CD4 (GTX85525, GeneTex), CD8 (GTX53126, GeneTex and anti-NKG2D (bs-0938R, Bioss) by the standard manufacturer's procedures using automated Leica Bond III-autostainer. DAB was applied and incubated to visualize the signals of the antibody staining. Hematoxylin was used as counterstain. Numeration of staining positive cells was performed in 4 random high-power fields of the tumor sections×400 magnification, and expressed as average cell number per field.

TUNEL Assay

The MBT-2-luc tumor sections were used to detect DNA fragmentation. DNA fragmentation in apoptotic cells was detected by terminal deoxynucleotidyl transferase (TdT)-mediated dUTP nick end labeling (TUNEL). following the manufacturer's protocol. (TUNEL BrightGreen Apoptosis Detection Kit, Vazyme Biotec, Nanjing, Jiangsu, China). All images were obtained using a microscope (Nikon Eclipse 80i) with an attached CCD camera.

IFN-γ Quantification by ELISA

IFN-γ level in culture medium of effector lymphocytes isolated from the MBT-2-luc tumor bearing mice of different treated groups, stimulated by the co-culture of target xenogeneic cells or MBT-2-luc cells for 2 days was evaluated using an enzyme-linked immunosorbent assay kit (BioLegend) according to the manufacturer's protocol. Effector cells with co-culture served as a baseline control. Relative IFN-γ activation of effector cells stimulated by co-cultured target cells was calculated as follows: ([IFN-γ] co-culture−[IFN-γ] baseline)/([IFN-γ] baseline)×100.

Statistical Analysis

Statistical analysis was performed using PASW Statistics 18. Graphs represent mean values±standard error of the mean. P-values were calculated using Students t-test for comparing two groups. Survival analysis was determined by the log-rank test. P<0.05 was considered statistically significant.

Results

Figure 1B:
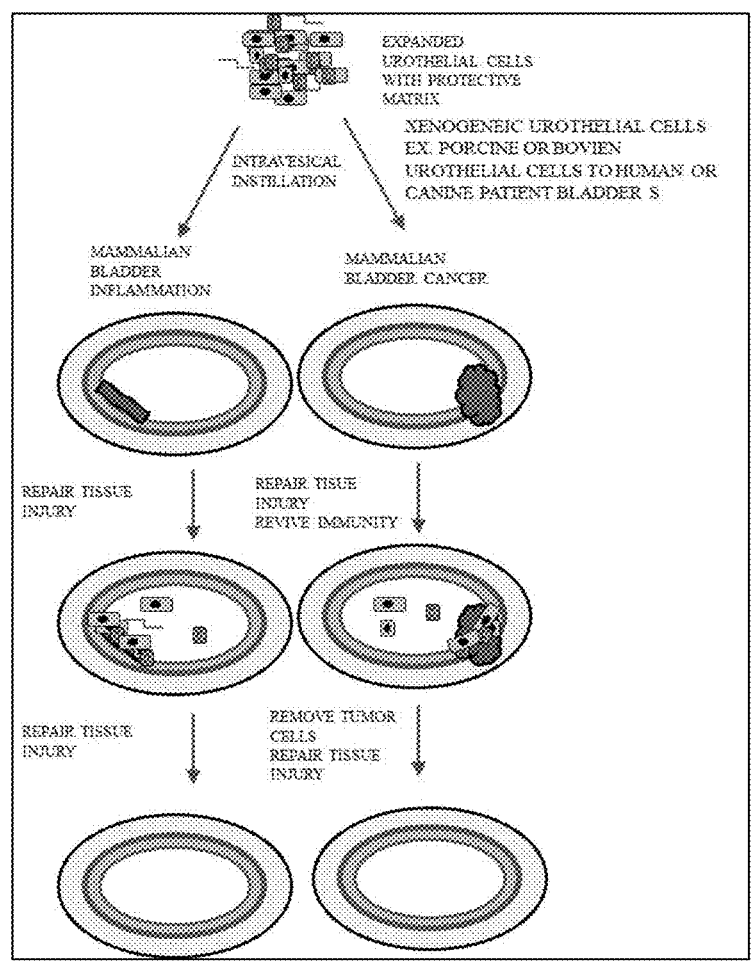
FIG. 1B is a schematic diagram of a preferred embodiment of the invention on the intravesical cell therapy by instilling the xenogeneic urothelial cells into bladder with cystitis or urothelial carcinoma.

A schematic graph illustrating an exemplary protocol for isolating and expanding urothelial cells with a biomimetic culture method for intravesical cell therapy is shown in FIG. 1A and a schematic diagram of a preferred embodiment of the invention on the intravesical cell therapy by instilling the xenogeneic urothelial cells into bladder with cystitis or urothelial carcinoma is shown in FIG. 1B.

Expanded PUCs express urothelial progenitor/stem cell markers: cytokeratin 5 (CK5) and cytokeratin 14 (CK14)

Figure 3:
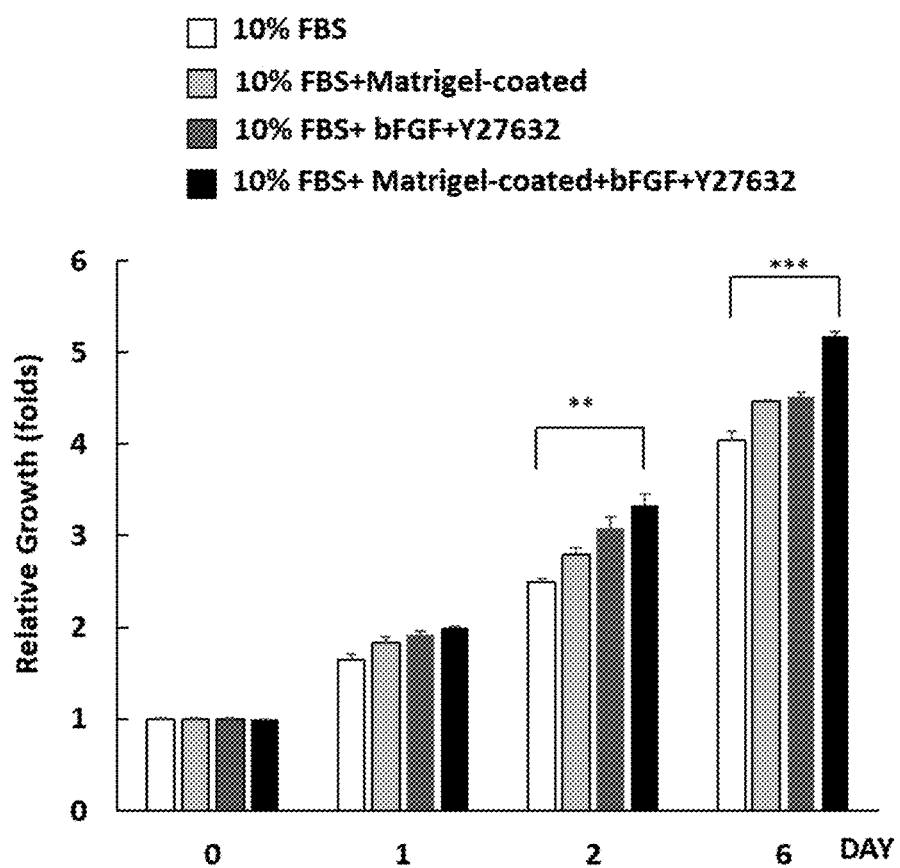
FIG. 3. The effects of different culture conditions on porcine urothelial cell growth. Cells were cultured either on Matrigel-coated 96 well plate, treated with bFGF (10 µg/ml)+Y27632 (10 µM) combination or Matrigel-coated plate with bFGF+Y27632 treatment plates for 1, 2 and 6 days. At different time points, the cell viability were measured by XTT assay. Data are presented as mean±SD. P<0.01, *P<0.001 relative to the 10% FBS only group. Y27632 is a ROCK inhibitor.

To test the therapeutic hypothesis, the urothelial cells were isolated from porcine bladder urothelium and expanded. The images of PUC at passage 1 and 5 were shown in FIGS. 2A and 2B. The urothelial stem/progenitor cell markers: CK5 and CK14, which are cytokeratin proteins and co-express within the urothelial stem/progenitor cells were used to characterize the expanded PUCs. Western blotting assay (FIG. 2C) and immunofluorescent staining (FIG. 2D) of PUCs revealed that both CK5 and CK14 are expressed in PUC cells. Next, we further to examine the proliferative potential of UPC by culturing in different ingredients of medium and environment. The results showed that the proliferative fold was increased when PUC cultured on the Matrigel coated-plate. Moreover, cells cultured on Matrigel-coated plate, and treated with FBS, bFGF and Y27632 given the highest proliferative potential (FIG. 3).

Intravesical PUC Instillation Attenuates CPP-Induced Cystitis

Figure 4A:
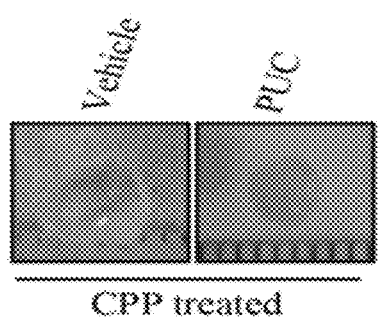
FIG. 4. Cyclophosphamide-induced cystitis with changes of the urothelium and intravesical installation of PUC attenuates CPP induced cystitis. The mice were intraperitoneally injected with 300 mg/kg CPP (300 mg/kg) and then PUCs ($10^6$ cells/100 µl) or vehicle control was intravesically instilled into the bladders 4 h after the CPP injection, the bladder morphology, weight, and H&E staining were performed after 24 h. (A) Representative images of the mouse bladders on day 1 after cyclophosphamide injection from the vehicle control and PUC-treated groups. The obvious congestion, enlargement and hemorrhaging in the bladder of CPP-treated mice of vehicle control group, but not in the PUC-treated group. (B) Bladder weight/body weight ratio in the control and PUC-treated groups. (C) Representative histological changes of the hematoxylin-eosin-stained bladder sections. Urothelium in the vehicle controls shows some remaining urothelial cells, and denuded areas. (D) Edema index of the bladder sections of vehicle control and PUC-treated mice. The data represent the mean±SD of three independent experiments. Scale bars represent 50 µm. P<0.01 versus the vehicle control. CPP: cyclophosphamide; H&E: hematoxylin and eosin FIG. 5. Intravesical instillation of PUC reduces urothelial injury. (A) representative images of IHC stained Ki-67 on bladder sections from vehicle control and PUC-treated groups. (B) Quantification of urothelial cell proliferation post CPP injection and treatment. Ki-67-positive cells are shown as a percent of total cells 24 h after injection of CPP (C). Representative TUNEL staining images of bladder sections. (D) Alcian blue staining of GAG layers. Arrows indicate the GAG layers. Dotted lines demarcate the border between urothelium and lamina propria. Data are presented as mean+SD and significance was calculated by an unpaired Student's t-test. *P<0.01 versus the vehicle control. Scale bars represent 50 µm. GAG: glycosaminoglycan; L: bladder lumen; TUNEL: terminal deoxynucleotidyl transferase (TdT)-mediated dUTP nick end labeling FIG. 6. The anti-tumor effect of intravesical xenogeneic urothelial cell immunotherapy, GC chemotherapy and combined therapy in MBT-2-luc orthotopic graft bladder tumor model. The tumor bearing mice were enrolled when tumor bioluminescent signal reached $10^5$ total plex and treated according to the treatment scheme (A). The representative IVIS imagines of tumor-bearing mice before and after treatments were shown (B). Kaplan-Meier progressive free survival curve (C) and total survival curve (D) of mice bearing tumors with different treatment groups across 3 independent studies were calculated by was performed by Sigma Plot 13 and compared with log-rank test. P value is shown for combined therapy versus xenogeneic urothelial cell immunotherapy and chemotherapy.
Figure 4B:
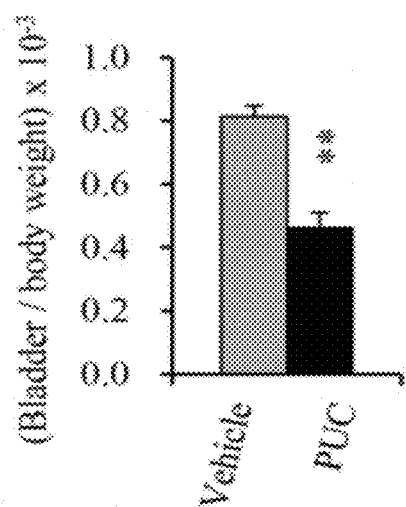
Figure 4C:
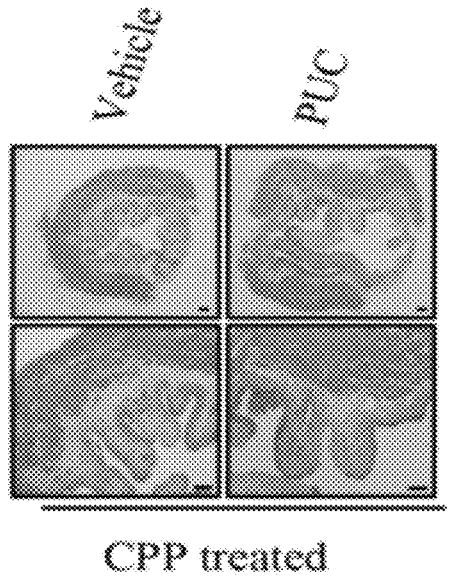
Figure 4D:
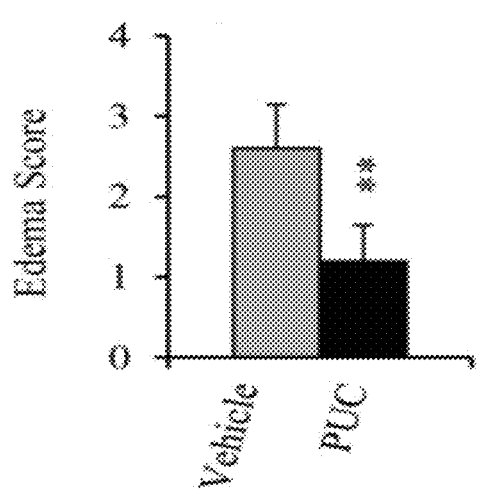

To demonstrate the therapeutic effect of intravesical instillation of PUCs on hemorrhagic cystitis, the CPP-induced cystitis mouse model, which has been widely used as an animal model of urothelial injury and hemorrhagic cystitis. The CPP-injected female mice were divided into two groups, the control group received the vehicle control and the treatment group was given $10^6$ PUCs at 4 h after CPP injection and all mice were sacrificed at 24 h post injection of CPP for experiments. Compared with the vehicle treated controls, the results showed that intravesical PUC treatment rescued the injuries caused by CPP injection with reduced bladder hemorrhages, congestion and weight (FIGS. 4A and 4B). Moreover, the histological analysis of bladder HE stained sections also showed that the edema of the lamina propria was lower and less exfoliation was observed (FIGS. 4C and 4D) in the PUC-treated group. These results suggest that intravesical administration of PUCs could protect the urothelium from attacks by noxious chemicals to reduce urothelial injury.

Intravesical PUC Instillation Represses CPP-Induced Urothelial Injury

Figure 5A:
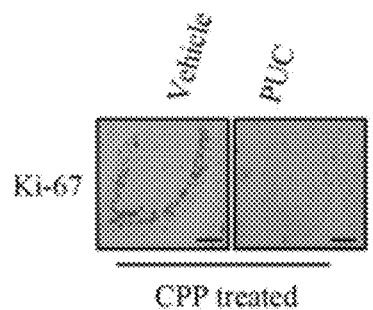
Figure 5C:
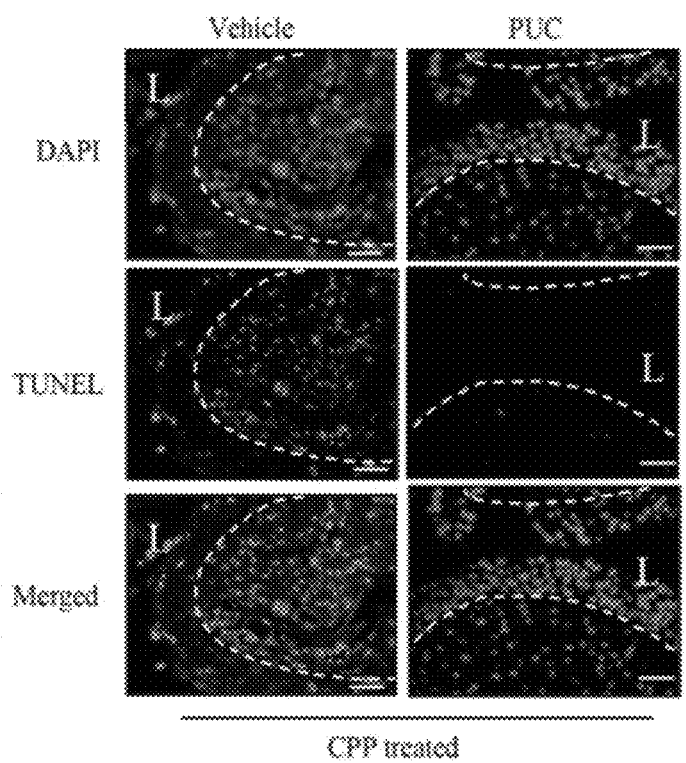
Figure 5B:
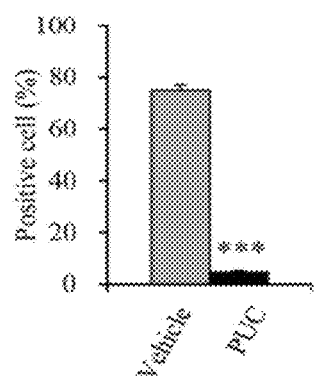
Figure 5D:
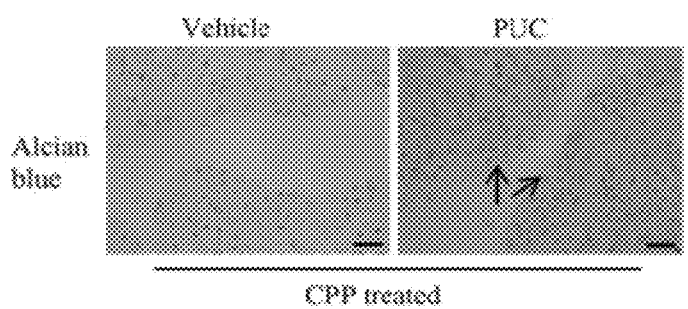

The proportion of Ki-67-positive cells in urothelium was significantly lower in PUC-treated group compared with vehicle-treated group 24 h after CPP injection (FIGS. 5A and 5B), suggesting that injury-induced proliferation in basal urothelial cells was decreased by PUCs. To assess the effect of intravesical instillation of PUCs on cell damage inflicted by CPP, the TUNEL assay was used to detect apoptotic cells caused by CPP. The results showed that CPP-induced apoptotic cells were observed in both urothelial cells in the urothelium and the stromal cells in the lamina propria, but intravesical PUC treatment markedly decreased the apoptotic cells compared with the vehicle controls (FIG. 5C). Alcian blue staining was performed to study the urothelial integrity affected by CPP treatment. The result showed the superficial layer of GAGs was preserved in the PUC-treated group, but was absent in vehicle control-group (FIG. 5D). These results indicated that intravesical PUC treatment reduced CPP-induced cell proliferation, cell apoptosis and maintained the urothelial integrity.

Figure 6A:
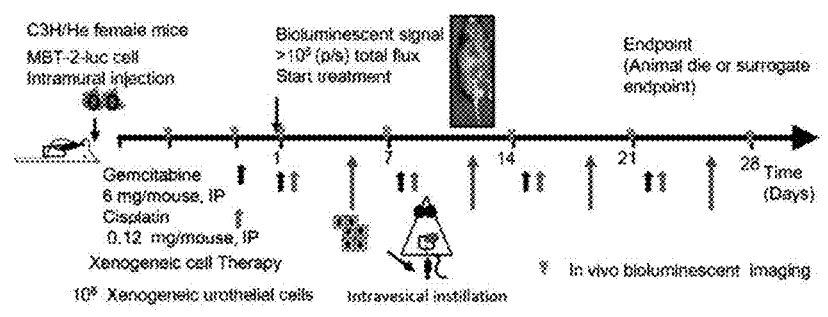
Figure 6B:
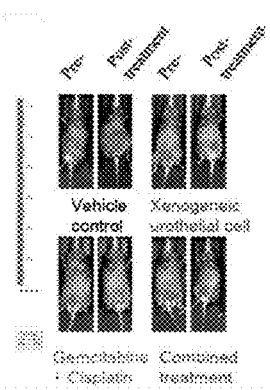
Figure 6C:
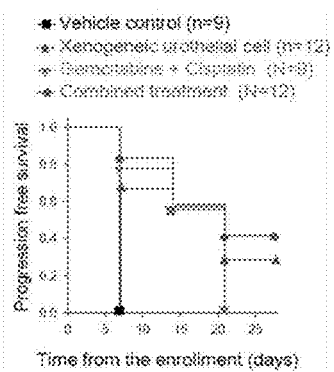
Figure 6D:
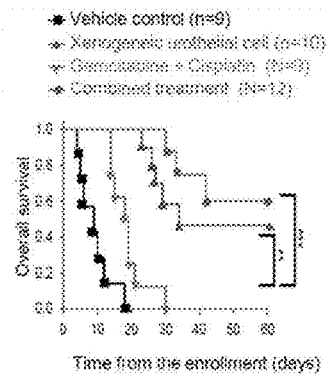

Intravesical Xenogeneic Urothelial Cell Immunotherapy and GC Chemotherapy Combined Treatment had a Synergistic Anti-Tumor Effect in the Orthotopic MBT-2-Luc Graft Bladder Tumor Mouse Model The orthotopic MBT-2-luc graft urothelial bladder tumor mouse model was used to evaluate the efficacy of the anti-tumor effects for xenogeneic urothelial cells as a therapy and in combination with standard cytotoxic chemotherapy. The experimental scheme was depicted in FIG. 6A. The results showed that comparing to the vehicle-treated groups, the tumor growth was significantly decreased in in all xenogeneic urothelial cells, GC, or combination treated-groups (FIG. 6B). Moreover, the progression free survival (FIG. 6C) and overall survival (FIG. 6D) were prolonged. Those treated with xenogeneic urothelial cells or combination showed about 30% and 40% durable response in progression free survival respectively and 45% and 60% in overall survival, respectively. Although xenogeneic urothelial cell immunotherapy or gemcitabine and cisplatin chemotherapy alone has anti-tumor activity, mice treated with both xenogeneic cell immunotherapy and GC chemotherapy exhibited a significant increase in tumor progressive free survival and total survival and combined treatment has highest survival. Xenogeneic cell treatment in both progressive and total survival all raised a tail of the curve, suggesting a more durable effect by xenogeneic cell immunotherapy than chemotherapy.

Figure 7A:
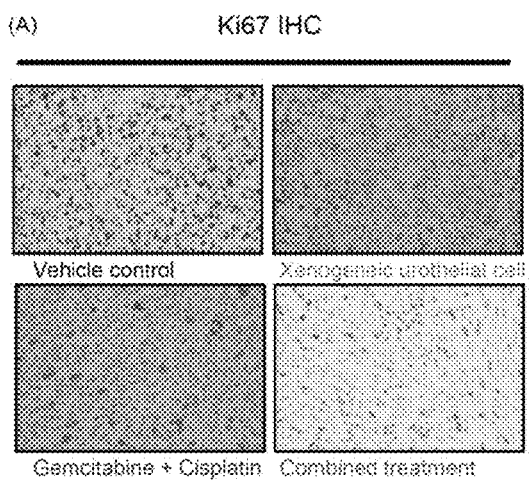
FIG. 7. The effects of intravesical xenogeneic urothelial cell immunotherapy, GC chemotherapy and combined therapy on tumor cell proliferation and survival in MBT-2-luc orthotopic graft urothelial bladder tumor model. Tumors from mice of different treatment groups were harvested, processed and sectioned for tumor cell Ki-67 IHC and TUNEL assay. Tumor sections were evaluated for cell proliferation 45 with Ki-67 IHC staining (A). Ki-67 positive cells on tumor sections were counted and quantified from mice of 3 independent experiments (B). Tumor sections were stained with TUNEL (FITC) and observed under a fluorescent microscope (C). DAPI was used for nuclear staining. TUNEL positive cells on tumor sections were counted and quantified from mice of 3 independent experiments (D). Values are expressed as mean±standard error of the mean (n=3). *p<0.05; p<0.01; *p<0.001, by Student's t test. Scale bar, 50 µm.
Figure 7B:
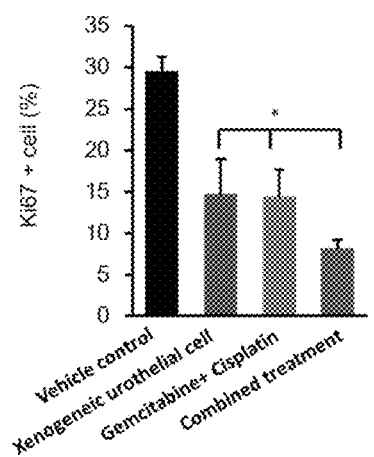
Figure 7C:
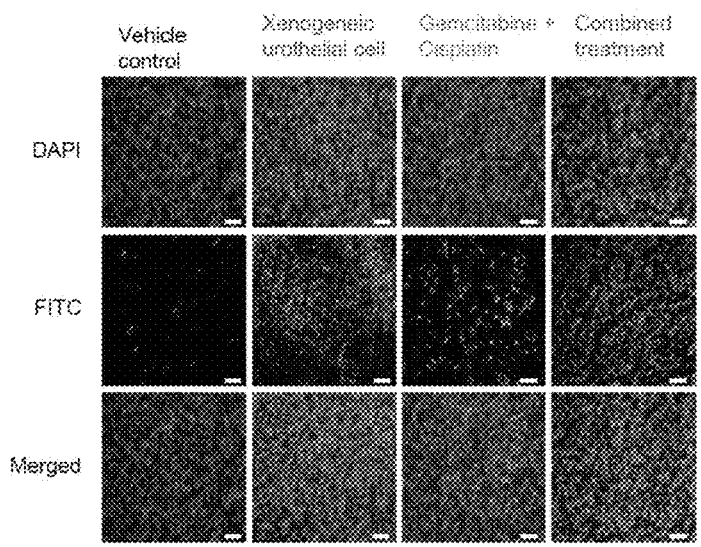
Figure 7D:
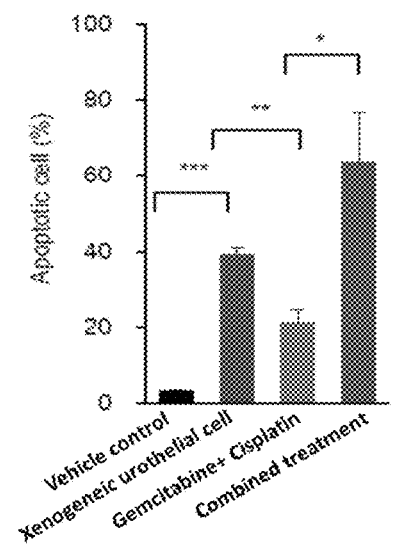

Intravesical Xenogeneic Urothelial Cell Immunotherapy, GC Chemotherapy and Combined Treatment Decrease Tumor Cell Proliferation and Increased Tumor Cell Apoptosis Further to demonstrate the anti-tumor effects of xenogeneic urothelial cell immunotherapy, GC chemotherapy and combined treatment, the tumors were fixed and sectioned for Ki-67 IHC staining and TUNEL assay to determine cell proliferation and cell death, respectively. The results showed that the Ki-67-positive tumor cells in all treated groups were less than untreated control. In addition, the proliferative tumor cells were lowest in the combined treatment group (FIGS. 7A and 7B). On the contrary, the results of TUNEL assay exhibited the increase of apoptotic cells in tumor tissues in all treatment group, especially in the combined treatment group. No matter single xenogeneic urothelial cell immunotherapy or combined treatment with chemotherapy, the effect of inducing tumor cell death was better than chemotherapy (FIGS. 7C and 7D).

Intravesical Xenogeneic Urothelial Cell Immunotherapy, GC Chemotherapy and Combined Treatment Enhanced Immune Cell Infiltration in Tumors To evaluate the impact of different treatments on intratumoral immune cell composition, T cell and NK cell infiltration into tumor were analyzed. Tumor T cell infiltration (CD4+ and CD8+ effector T cells) was increased in xenogeneic urothelial cell immunotherapy, GC treatment and the combined therapy (FIGS. 8A and 8B), which reflect effective immunotherapy. Quantitative results showed that compared to the vehicle-treated group tumors, xenogeneic urothelial cell treated tumors from single and combined treatment groups were found to have a significant increase in effector CD4+ T cell (FIG. 8D), CD4+ T cell (FIG. 8E) and NKG2D+NK cell (FIG. 8F) infiltration in tumors. However, the increased NK cell infiltration was not observed in tumors with GC treatment alone group (FIGS. 8C and 8F).

Figure 9A:
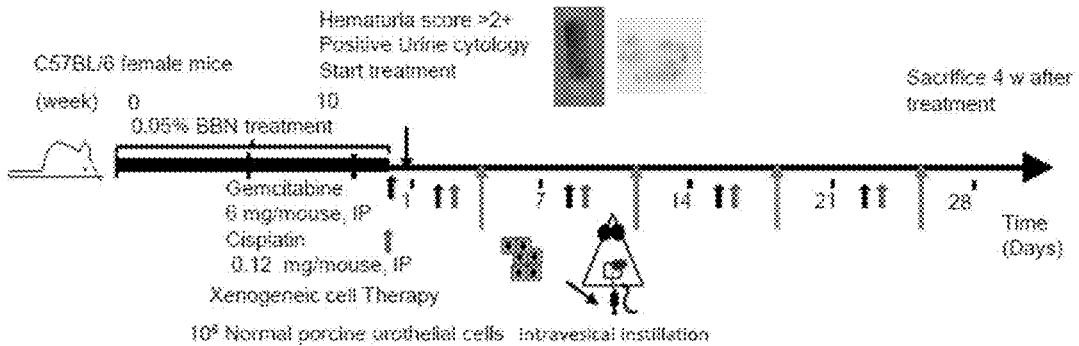
FIG. 9. The anti-tumor effect of intravesical xenogeneic urothelial cell immunotherapy, GC chemotherapy and combined therapy in the BBN-induced bladder tumor mouse model. Tumor-bearing mice were treated according to the experimental scheme (A). Representative photographs of the gross tumors from mice with different treatments (B). Tumor weights of the different treatment groups (C) (mean±SD, at least 9 mice from 3 independent experiments). Representative H&E stained images of tumors of different treatment groups (D). Histograms of the pathological analysis for the proportions of hyperplastic and neoplastic changes in bladder H&E stained section of mice with different treatments (E). *p<0.05; **p<0.01 by Student's t test.
Figure 9B:
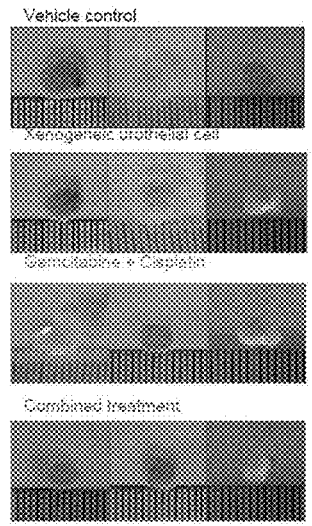
Figure 9C:
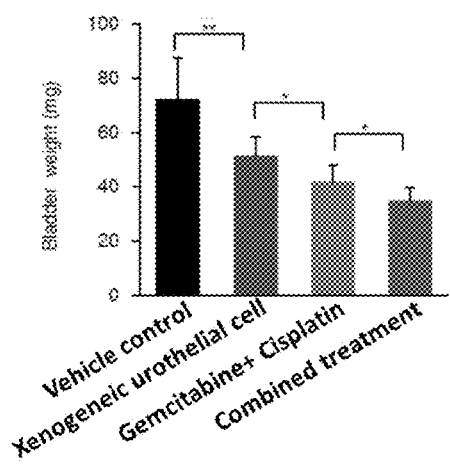
Figure 9D:
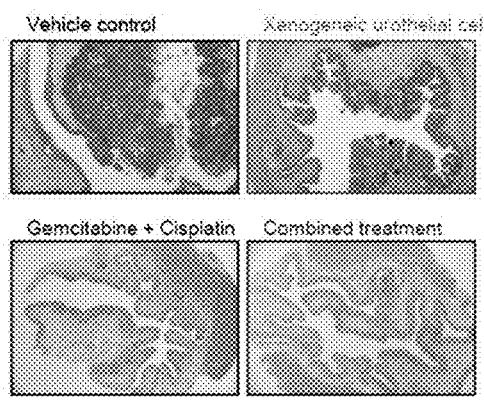
Figure 9E:
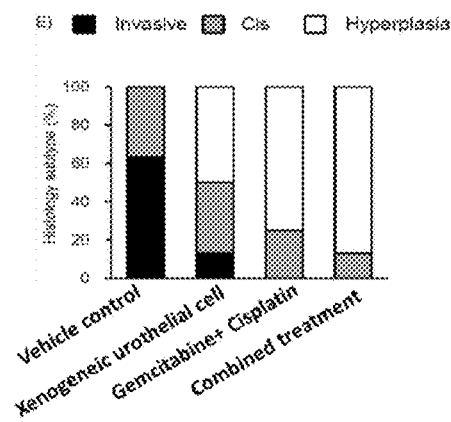

Intravesical Xenogeneic Urothelial Cell Immunotherapy and Gemcitabine Plus Cisplatin Chemotherapy Combined Treatment Synergistically Delay Tumor Progression in the BBN-Induced Bladder Tumor Mouse Model To test the anti-tumor effects of intravesical xenogeneic cell therapy in combination with chemotherapeutic agents in delaying tumor progression, BBN-induced tumor mouse model, which simulates the human bladder tumorigenesis from hyperplasia, carcinoma in situ (CIS) to invasive carcinoma was used. The BBN-induced bladder tumor bearing mice were divided into 4 treatment groups: (i) vehicle control, (ii) xenogeneic urothelial cell: intravesical of instillation xenogeneic xenogeneic urothelial cell cells ($1 \times 10^6$ cells), once a week, day 3 for 4 weeks, (iii) Gemcitabine plus cisplatin (GC) chemotherapy: intraperitoneal injection (IP) of gemcitabine (6 mg/mouse, day 1) and cisplatin (0.12 mg/mouse, day 2) once a week, for 4 weeks, and (iv) combined treatment. The progression of BBN-induced bladder tumors in the treatment groups and control group was assessed by macroscopic and histopathological examination from harvested bladders. The experimental scheme was depicted in FIG. 9A. The results demonstrated that intravesical xenogeneic urothelial cell immunotherapy, GC treatment alone or in combination of chemotherapy significantly reduced the tumor weight. Furthermore, the combined treatment achieved highest decrease in tumor weight (FIGS. 9B and 9C). Consistently with this macroscopic difference, histopathological analysis also showed significantly lower proportion of mice progressed to invasive carcinoma in the xenogeneic cell, GC treated group, and in combination therapy (FIGS. 9D and 9E).

Figure 10A:
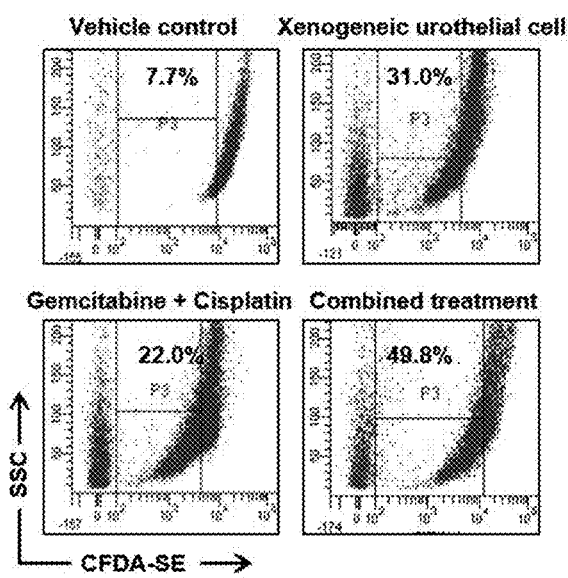
FIG. 10. The immune activation on reactive T cell proliferation in MBT-2-lu-tumor bearing mice by different treatments. The mixed lymphocyte reaction was performed using lymphocytes isolated from the spleens of mice with different treatments. Lymphocytes were labeled with CFDA-SE and co-culture with xenogeneic urothelial cells or MBT-2-luc cells. Proliferation of CFDA-SE labelled cells was measured by FACS analysis after 2 days culture. CFDA-SE labelled lymphocyte division was monitored with CFDA-SE labeling on cells to $5\times10^5$ lymphocytes effector cells cultured with $1\times10^5$ target xenogeneic cells or tumor cells. Flow cytometry analysis profiles of CFDA-SE-labeled lymphocytes after 2 days culture with xenogeneic urothelial cells (A) or MBT-2-luc cells (C). Percentage of proliferating lymphocytes responding to xenogeneic urothelial cells harvested on day 2 after treatment initiation (D). Percentage of proliferating lymphocytes responding to MBT-2-luc cells (D). *p<0.05; p<0.01; *p<0.001, by Student's t test. Means of are shown±SD and represent 4 separate experiments.
Figure 10B:
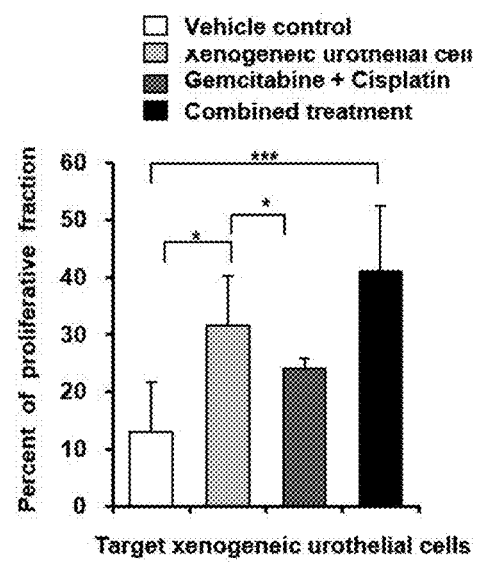
Figure 10C:
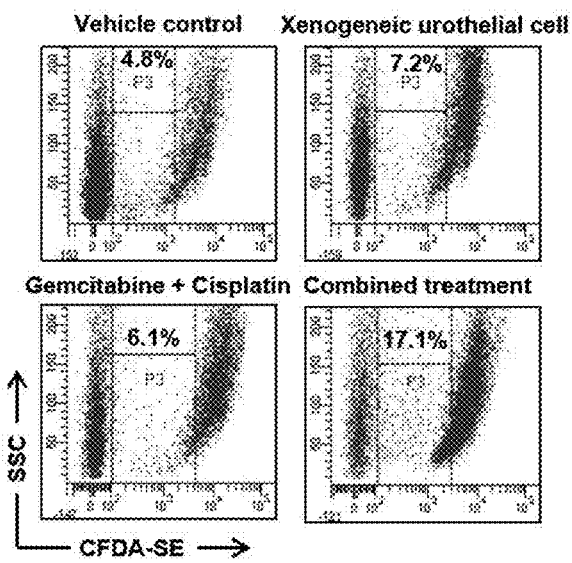
Figure 10D:
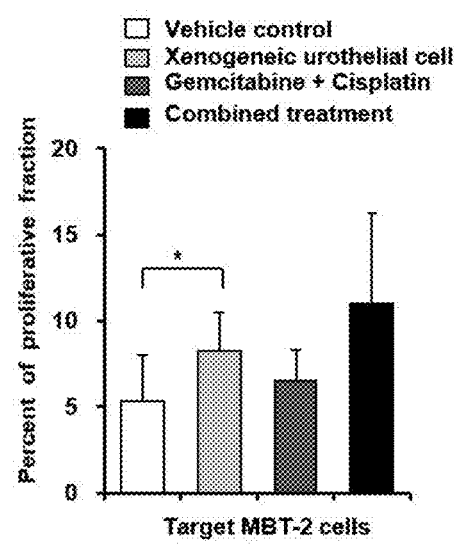

Intravesical Xenogeneic Urothelial Cell Immunotherapy, GC Chemotherapy and Combined Treatment Activated Immune Responses The hypothesis of the xenogeneic cell immunotherapy could induce immune response due to xenorejection and collaterally increase anti-tumor immune responses. To examine whether T cells isolated from mice treated with xenogeneic cells could exhibit enhanced proliferative responses when co-cultured with xenogeneic urothelial cells or bladder tumor cells by mixed lymphocyte reaction (MLR) using carboxyfluorescein diacetate succinimidyl ester (CFDA-SE)-based proliferation assay. First, lymphocytes were isolated from spleen in MBT-2-luc tumor bearing mice with different treatments and then labelled with CFDA-SE. The labelled CFDA-SE lymphocytes were co-cultured with attached xenogeneic urothelial cells or tumor cells (effector/target cells ratio 5:1) for two days. After that, lymphocytes were then harvested and analyzed by flow cytometry analysis to measure the intensity of CFDA-SE fluorescence. The results showed that the effector lymphocytes stimulated by co-culturing with xenogeneic urothelial cells showed the proliferating proportion of lymphocytes (CFDA-SE low) from mice treated with xenogeneic urothelial cells was higher than that of mice treated with vehicle control, indicating that xenogeneic urothelial cell treated mice developed immune response to xenogeneic cells (FIGS. 10A and 10B). Moreover, the effector lymphocytes from mice treated xenogeneic urothelial cells also showed higher proliferating proportion when stimulated with MBT-2-luc bladder tumor cells (FIGS. 10C and 10D). Increased lymphocyte proliferation was also found in combined treatment mice, indicating xenogeneic urothelial cell treatment induces immune responses in tumor-bearing mice to both implanting xenogeneic urothelial cells and tumor cells.

Figure 11A:
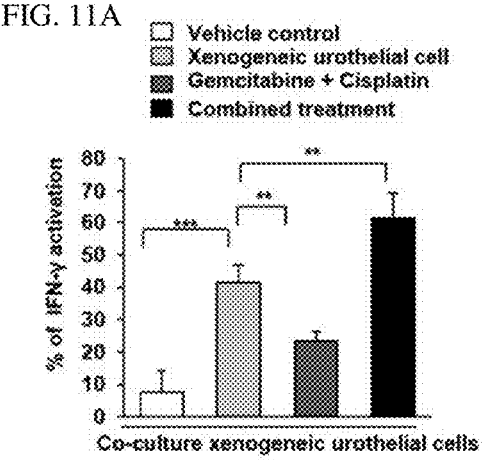
FIG. 11. The stimulatory activity on reactive T cell cytokine production and cytotoxicity in MBT-2-lu-tumor bearing mice by different treatments. IFNγ level in supernatants collected after 2 days of co-culture of lymphocytes isolated from spleens of mice with 46 different treatments with xenogeneic urothelial cells or MBT-2-luc cells was measured by ELISA. The supernatants of lymphocytes culture alone were used as the baseline control. Relative stimulatory activity of xenogeneic urothelial cells (A) and MBT-2-luc (B) on IFNγ production by lymphocytes from mice of different treatment group was calculated as the following: ([IFNγ]co-cultured-[IFNγ]baseline)/([IFNγ]baseline). IFNγ level in the supernatant of lymphocytes culture alone was used as the baseline. Effector lymphocytes ($1 \times 10^6$) from spleens of mice of different treatment groups were added into the plate seeded with $1 \times 10^5$/well of target CFDA-SE labelled effector xenogeneic urothelial cells (C&D) or MBT-2-luc (E&F) and co-cultured for 4 hours. At the end of co-culture, suspension effector cells in the wells were washed out and the intensity of CFDA-SE labelled target cells was measured. Representative fluorescent images of wells added with lymphocytes from mice with different treatments targeting xenogeneic urothelial cells (C) and MBT-2-luc cells (E). The relative cytotoxic activity of lymphocytes was determined following the formula: (RFU-exp-RFUctrl)/RFUctrl. The intensity of CFDA-SE labelled target without adding lymphocytes was set as controls. Quantitation of effector lymphocyte cytotoxicity to target xenogeneic urothelial cells (D) and MBT-2-luc cells (F). *p<0.05; p<0.01; *p<0.001, by Student's t test.
Figure 11B:
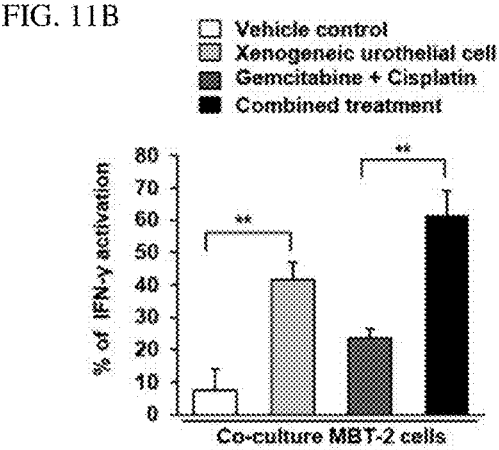
Figure 11C:
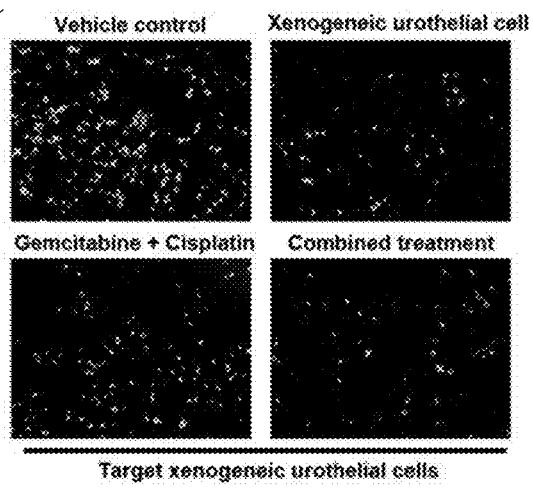
Figure 11D:
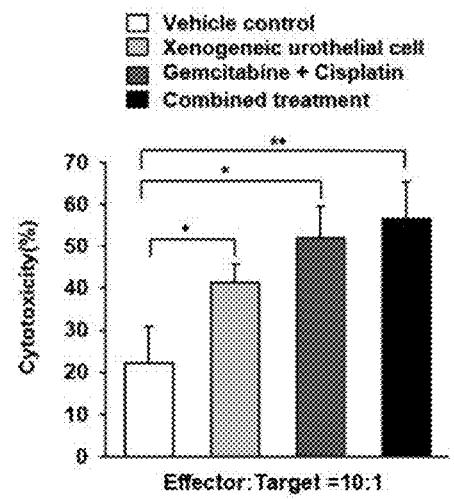
Figure 11E:
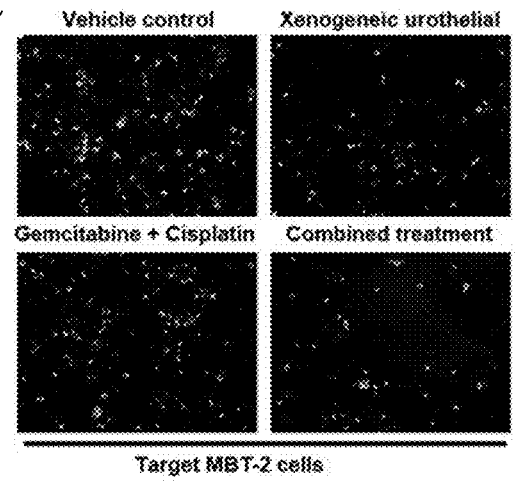
Figure 11F:
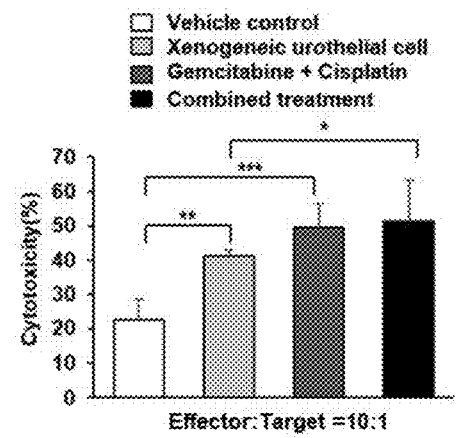

Intravesical Xenogeneic Urothelial Cell Immunotherapy, GC Chemotherapy and Combined Treatment Increased Effector Immune Cell Functions The production of effector cytokines (IFNγ), which plays an essential role in anti-tumor immunity in immune cells was evaluated. Lymphocytes isolated from the spleens of tumor-bearing mice with different treatments were co-cultured with either xenogeneic urothelial cells or MBT-2-luc cells, and then determine the IFN-γ activation in the co-cultured conditioned medium. The results showed no matter co-cultured with xenogeneic urothelial cells or tumor MBT-2-luc cells, IFNγ activation was higher both in lymphocytes isolated from xenogeneic urothelial cell immunotherapy alone and in combined treatment with chemotherapy (FIGS. 11A and 11B). The increase in effector cytokine production by treatments correlated with the changes in effector cell proliferation, indicating that the implantation of xenogeneic urothelial cells regulates effector cell function. Nevertheless, effector cell subpopulation involved in xenogeneic urothelial cell-induced cell activation for anti-tumor response in mice is needed to be determined. That more T cells exhibited effector characteristics was confirmed by T cell proliferation and more activation of IFN-γ production than control-treated mice upon restimulation in vitro with xenogeneic urothelial cells or MBT-2-luc cells. To demonstrate whether xenogeneic urothelial cell immunotherapy could affect T cells' cytotoxic activity function, the immune effector cell-mediated target cell cytotoxicity assay was carried on. The effector lymphocytes isolated from spleens with different treatment were co-cultured with CFDA-SE labeled target cells, which were xenogeneic urothelial cells or MBT-2-luc cells and then detect the T cells' cytotoxic activity function by measuring the fluorescent intensity of remained CFDA-SE labelled cells. The results showed the highest cytotoxic activity to either target xenogeneic urothelial cells or MBT-2-luc cells was noted in the group of mice receiving combined treatment. Xenogeneic urothelial cell treatment had significantly activation of cytotoxic cells and GC treatment also increased the cytotoxicity to target both xenogeneic urothelial cells or MBT-2-luc cells (FIG. 11C-F).

REFERENCES

1. Torre L A, Siegel R L, Ward E M, Jemal A: Global Cancer Incidence and Mortality Rates and Trends—An Update. Cancer Epidemiol Biomarkers Prev 2016, 25(1):16-27.
2. Wu X R: Urothelial tumorigenesis: a tale of divergent pathways. Nat Rev Cancer 2005, 5(9):713-725.
3. Oxford G, Theodorescu D: The role of Ras superfamily proteins in bladder cancer progression. J Urol 2003, 170(5):1987-1993.
4. Jones T D, Wang M, Eble J N, MacLennan G T, Lopez-Beltran A, Zhang S, Cocco A, Cheng L: Molecular evidence supporting field effect in urothelial carcinogenesis. Clin Cancer Res 2005, 11(18):6512-6519.
5. Sidransky D, Frost P, Von Eschenbach A, Oyasu R, Preisinger A C, Vogelstein B: Clonal origin bladder cancer. N Engl J Med 1992, 326(11):737-740.
6. Lutzeyer W, Rubben H, Dahm H: Prognostic parameters in superficial bladder cancer: an analysis of 315 cases. J Urol 1982, 127(2):250-252.
7. Burger M, Oosterlinck W, Konety B, Chang S, Gudjonsson S, Pruthi R, Soloway M, Solsona E, Sved P, Babjuk M et al: ICUD-EAU International Consultation on Bladder Cancer 2012: Non-muscle-invasive urothelial carcinoma of the bladder. Eur Urol 2013, 63(1):36-44.
8. Morales A, Eidinger D, Bruce A W: Intracavitary Bacillus Calmette-Guerin in the treatment of superficial bladder tumors. J Urol 1976, 116(2):180-183.
9. Alexandroff A B, Jackson A M, O'Donnell M A, James K: BCG immunotherapy of bladder cancer: 20 years on. Lancet 1999, 353(9165):1689-1694.
10. Bohle A, Brandau S: Immune mechanisms in bacillus Calmette-Guerin immunotherapy for superficial bladder cancer. J Urol 2003, 170(3):964-969.
11. Botteman M F, Pashos C L, Redaelli A, Laskin B, Hauser R: The health economics of bladder cancer: a comprehensive review of the published literature. Pharmacoeconomics 2003, 21(18):1315-1330.
12. Mariotto A B, Yabroff K R, Shao Y, Feuer E J, Brown M L: Projections of the cost of cancer care in the United States: 2010-2020. J Natl Cancer Inst 2011, 103(2):117-128.
13. Grover S, Srivastava A, Lee R, Tewari A K, Te A E: Role of inflammation in bladder function and interstitial cystitis. Ther Adv Urol 2011, 3(1):19-33.
14. Talar-Williams C, Hijazi Y M, Walther M M, Linehan W M, Hallahan C W, Lubensky I, Kerr G S, Hoffman G S, Fauci A S, Sneller M C: Cyclophosphamide-induced cystitis and bladder cancer in patients with Wegener granulomatosis. Ann Intern Med 1996, 124(5):477-484.

What is claimed is:

1. A method for treating a subject suffering from urothelial carcinoma, or bladder cancer, comprising administering intravesically to the subject an effective amount of a composition comprising xenogeneic urothelial cells in a solution wherein the xenogeneic urothelial cells are urothelial stem cells, urothelial progenitor cells, urothelial precursor cells and mature urothelial cells.

2. The method of claim 1, wherein the composition comprising xenogeneic urothelial cells is administered in combination with a pharmaceutically effective amount of one or more chemotherapy drugs.

3. The method of claim 2, wherein the one or more chemotherapy drugs are selected from the group comprising of an alkylating agent, a nitrosourea agent, an antimetabolite, an antitumor antibiotic, an alkaloid derived from a plant, a topoisomerase inhibitor, a hormone therapy medicine, a hormone antagonist, an aromatase inhibitor, a P-glycoprotein inhibitor and a platinum complex derivative.

4. The method of claim 1, wherein tumor proliferation is suppressed and tumor cell death is increased.

5. The method of claim 1, wherein the xenogeneic urothelial cells is selected from human, porcine, bovine, equine sources or other mammal sources.

* * * * *